(12) United States Patent
Knüttel

(10) Patent No.: US 10,393,501 B2
(45) Date of Patent: Aug. 27, 2019

(54) DEVICE FOR DETERMINING A 3D STRUCTURE OF AN OBJECT

(71) Applicant: Voco GmbH, Cuxhaven (DE)

(72) Inventor: Alexander Knüttel, Viernheim (DE)

(73) Assignee: VOCO GMBH, Cuxhaven (DE)

(*) Notice: Subject to any disclaimer, the term of this patent is extended or adjusted under 35 U.S.C. 154(b) by 249 days.

(21) Appl. No.: 15/584,216

(22) Filed: May 2, 2017

(65) Prior Publication Data

US 2017/0322015 A1 Nov. 9, 2017

(30) Foreign Application Priority Data

May 4, 2016 (EP) ..................................... 16168338

(51) Int. Cl.
| | |
|---|---|
| *G01B 9/02* | (2006.01) |
| *G01B 11/24* | (2006.01) |
| *G01N 21/47* | (2006.01) |
| *G03H 1/04* | (2006.01) |
| *G03H 1/00* | (2006.01) |

(52) U.S. Cl.
CPC ..... *G01B 9/02047* (2013.01); *G01B 9/02007* (2013.01); *G01B 9/02059* (2013.01); *G01B 11/2441* (2013.01); *G01N 21/4795* (2013.01); *G03H 1/0443* (2013.01); *G03H 1/0465* (2013.01); *G03H 2001/0033* (2013.01); *G03H 2210/30* (2013.01); *G03H 2222/13* (2013.01)

(58) Field of Classification Search
CPC ............ G01B 9/02047; G01B 9/02007; G01B 9/02059; G01B 11/2441; G01N 21/4795; G03H 1/0443; G03H 1/0465; G03H 2001/0033; G03H 2210/30; G03H 2222/13

See application file for complete search history.

(56) References Cited

U.S. PATENT DOCUMENTS

| | | | | |
|---|---|---|---|---|
| 3,580,656 | A | * | 5/1971 | Carson ..................... G03H 1/02 359/21 |
| 5,856,965 | A | * | 1/1999 | Tsuchiya ................ G11B 7/005 369/121 |
| 7,808,646 | B2 | | 10/2010 | Rembe et al. |

(Continued)

FOREIGN PATENT DOCUMENTS

| | | |
|---|---|---|
| DE | 102007010387 A1 | 9/2008 |
| EP | 2796938 A1 | 10/2014 |

*Primary Examiner* — Christine S. Kim
(74) *Attorney, Agent, or Firm* — Bose McKinney & Evans LLP

(57) ABSTRACT

A device for determining a 3D structure of an object having first and second laser emitters which generate laser radiation with first and second different wavelengths, respectively. A first beam splitter splits the laser radiation of each laser emitter into reference and illuminating radiation. The illuminating radiation is adapted to impinge on the object to be measured, be reflected by the object as object radiation, and interfere with the reference radiation to form interference patterns. A detector receives the interference patterns. A selection hologram deflects object radiation which impinges on it within a predefined incidence angle range and passes object radiation which impinges on it outside of the incidence angle range undiffracted. The undiffracted radiation either passes by the determination area of the detector or impinges on the determination area at an angle outside the determination angle range.

24 Claims, 4 Drawing Sheets

(56) References Cited

U.S. PATENT DOCUMENTS

| | | | |
|---|---|---|---|
| 8,068,235 B1* | 11/2011 | Marron | G03H 1/0443 |
| | | | 356/495 |
| 9,297,647 B2 | 3/2016 | Knüttel | |
| 2018/0365810 A1* | 12/2018 | Khare | G06T 5/003 |

* cited by examiner

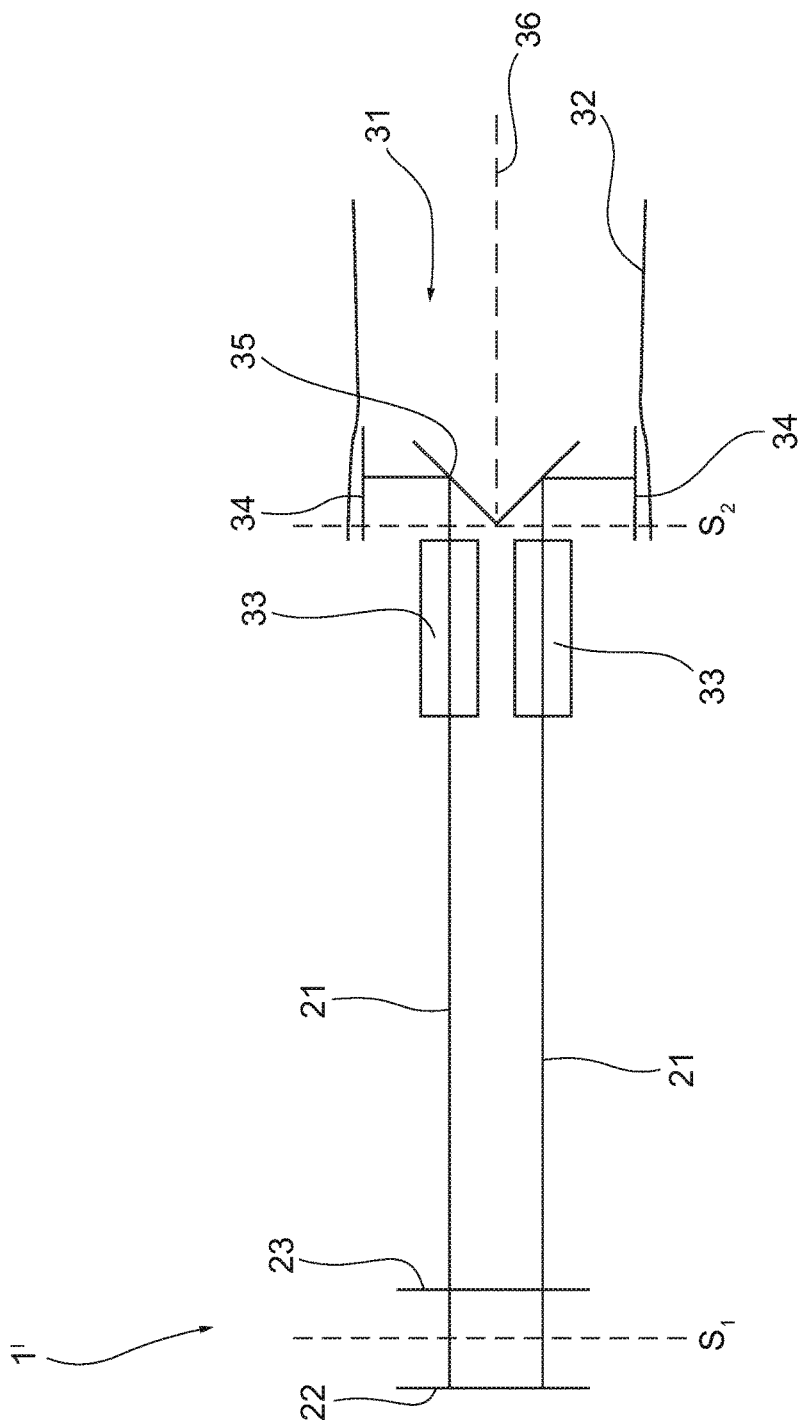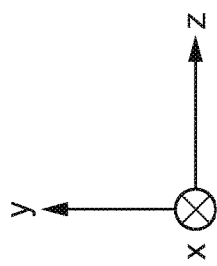
Fig. 3

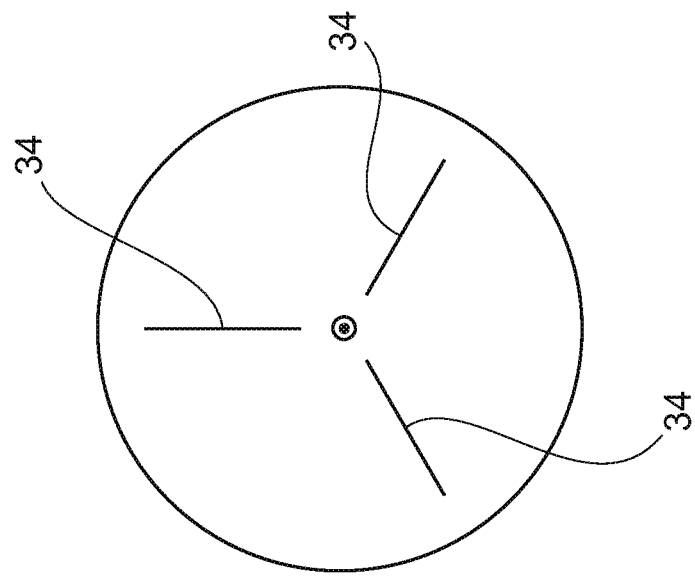
Fig. 4b
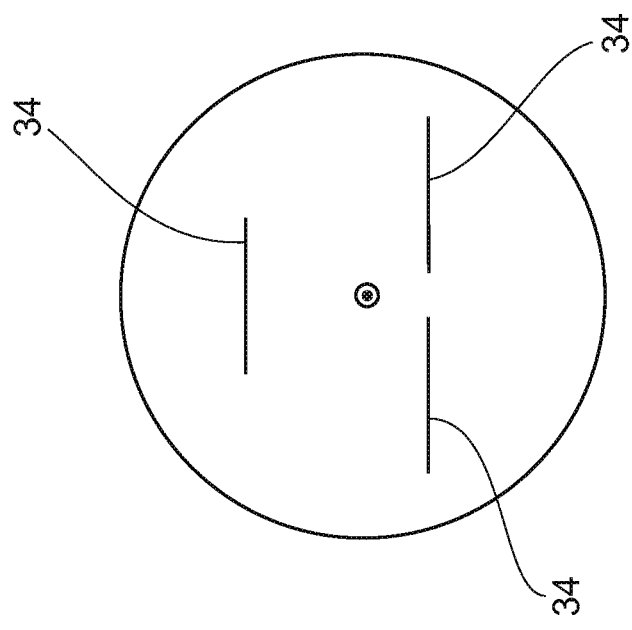
Fig. 4a
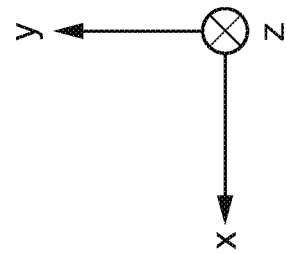

DEVICE FOR DETERMINING A 3D STRUCTURE OF AN OBJECT

RELATED APPLICATIONS

This application claims priority to EP 16 168 338.8, filed on May 4, 2016, the entire disclosure of which is hereby incorporated herein by reference in its entirety.

BACKGROUND

The present invention relates to a device for determining a 3D structure of an object, comprising a first laser emitter, which generates laser radiation with a first wavelength, and a second laser emitter, which generates laser radiation with a second wavelength. The two wavelengths differ from one another. The device furthermore comprises a first beam splitter, which divides the laser radiation of the laser emitters into a reference radiation and an illuminating radiation, the illuminating radiation impinging on the object to be measured, being reflected by the object as object radiation and interfering with a reference radiation. A detector detects the interference patterns resulting therefrom.

Such devices are used, for example, in dental technology for scanning individual teeth or whole dentures. For example, if a denture model of a patient is to be created, the scanning of the real denture can be performed completely without contact. The production of impressions directly on the patient is thus eliminated completely.

Such a device is known from EP 13 165 409. It works according to the principle of digital holography. At least two laser emitters emit laser radiation of different wavelengths. This is divided into a reference radiation and an illuminating radiation by means of a beam splitter. While the reference radiation is directed onto a detector via a mirror arrangement, the illuminating radiation impinges on the object to be detected. The illuminating radiation is reflected by the object as object radiation and also directed to the detector. Reference radiation and object radiation of one wavelength interfere with one another. The resulting interference patterns are recorded by the detector. If, for example, a tooth is to be measured three-dimensionally, speckle scattering light, which falls at least partially on the detector, is produced by the illuminating radiation and impinges on the rough surface of the tooth. Depending on the surface roughness and the scattering behavior below the surface, a portion of scattering light is also produced, which falsifies the measuring results as speckle noise.

SUMMARY

This disclosure teaches a device for detecting a 3D structure of an object, the measurements of which are less susceptible to scattered light and to the resulting speckle noise.

The device according to this disclosure for detecting a 3D structure of an object comprises at least two laser emitters, which generate laser radiation of a particular wavelength each. The wavelengths of the laser emitters are different. In a first beam splitter, the laser radiation of the emitters is divided into a reference radiation and an illuminating radiation, respectively. The illuminating radiation is directed to the object to be measured, reflected from the object as object radiation and then impinges on a detector. The reference radiation is directed directly to the detector and interferes there with the object radiation. An interference pattern is thus formed, which is detected by the detector.

The basic function of the device according to this disclosure is described in EP 2 796938 B1, which is hereby incorporated by reference in its entirety.

The device according to this disclosure has a selection hologram, which is designed to suitably deflect object radiation at a predetermined incidence angle range. Only the object radiation reflected by the object, which impinges on the selection hologram at a predefined incidence angle, is suitably deflected in such a manner that, on its further path, it impinges on a determination area of the detector. Object radiation which impinges on the selection hologram outside the incidence angle range leaves the selection hologram without being diffracted. It does not reach the determination area of the detector. This object radiation then passes by the determination area of the detector along its further path, in some cases even past the detector itself. Thus, the radiation impinges on the detector outside the determination area and consequently does not impinge on the determination area and sometimes not even on the detector.

Reference is made to the Figures and to the plane of the sheet used in the Figures for explaining the orientation of the incidence angles. In the present text, therefore, the term "vertical" is understood as "perpendicular to the plane of the sheet" and "horizontal" as "in the plane of the sheet," i.e., parallel to the detector or parallel to the determination area.

On the one hand, the incidence angle range preferably extends between the direction of the beam path, i.e., the direction of the illumination radiation, and the vertical. On the other hand, the incidence angle range also extends between the direction of the beam path and the horizontal. For example, the (vertical) incidence angle range between the direction of the beam path and the vertical may be significantly greater than the (horizontal) incidence angle range between the direction of the beam path and the horizontal. Preferably, it is several 100 mrad between the direction of the beam and the vertical, so that the object radiation, reflected by the object over the entire vertical, impinges on the detector.

In the context of this disclosure, the determination area of the detector is understood to be a partial area of a detection area. The detection area is the area in which the detector detects, i.e., takes note of incident radiation and can process it further. The determination area preferably is the inner partial area of the detection area. Radiation, which falls on the determination area, can be evaluated by the detector so that error-free detection of interference patterns is possible in practice. Radiation that impinges on the detection area of the detector outside of the determination area, i.e., on a marginal area of the detection area, does not allow for an interferometric detection. Into the bargain, this radiation impinges on the detector under such angular conditions that a sensible interference-capable signal cannot arise and thus no, at least no robust and error-free detection of interference patterns by the detector is possible. In other words, the object radiation must extend in the direction of the detector in a predetermined angular range (incidence angle range) in order to impinge on the determination area and not just on the detection area. Object radiation, which runs at incidence angles of more than 100 mrad, does not permit a meaningful and error-free evaluation when it impinges on the detector.

In addition, the radiation that impinges on the detector within the determination area has to impinge on the detector or the determination area within a specific angular range in order to produce a useful interference-capable signal, which makes a meaningful evaluation possible. The angular range, called determination angle range, is measured against the perpendicular on the surface of the determination area of the detector. The determination angle range preferably is smaller than the incidence angle range between beam direction and the horizontal. The determination angle range may preferably comprise angles less than 10°. The very preferred angular range is less than 8°. Radiation, which impinges on the determination area at an angle outside the determination angle range, cannot be evaluated reliably and robustly.

In a preferred embodiment, the device according to this disclosure comprises an evaluating unit, which evaluates radiation impinging on the determination area. In this case, preferably only the radiation is taken into account for an evaluation, which impinges within the determination angle range on the determination area of the detector. Radiation, which impinges on the detector or the determination area with an incidence angle outside the determination angle range, is not taken into account during the evaluation. The evaluation unit may be integrated in the detector, executed as a separate element or be contained in another element of the device.

Particularly preferably, the selection hologram is a volume hologram. It is designed in such a manner that only object radiation that fulfills the Bragg equation is suitably deflected, so that the object radiation, on its further path, impinges on the determination area of the detector. As is known by those of skill in the art, the Bragg equation is as follows:

$$n\lambda = 2d \sin \theta,$$

where n is an integer,
$\lambda$ is wavelength, and
$\theta$ is the angle of scattering.

If the Bragg equation is not fulfilled, the object radiation passes through the volume hologram without being diffracted. The Bragg equation, inter alia, connects the wavelength of the radiation with its incidence angle to the grating plane of the selection hologram. The predetermined incidence angle, in which the selection hologram directs the object radiation to the determination area of the detector, thus depends on the wavelength of the object radiation. In other words, a separate incidence angle range is defined for each wavelength of the laser radiation, in which the object radiation in question is deflected in the direction of the determination area. Preferably, the object radiation that is deflected by the selection hologram is deflected away from the detector. The angle of deflection preferably is 5° to 30°, particularly preferably 10° to 20°, and further preferably about 15°.

Advantageously, the device has a second beam splitter, which is arranged between the selection hologram and the detector. Object radiation that is deflected by the selection hologram impinges on the beam splitter and is reflected in the direction of the detector in such a manner that it falls on the determination area of the detector. The angle of inclination of the beam splitter preferably results from the angle of inclination of the selection hologram and from the fact that the radiation is to fall, as far as possible, perpendicularly to the detector. Preferably, the second beam splitter is arranged so that an angle of at most 45° is formed between the surface of the second beam splitter and the detector. Particularly preferably, the angle is less than or equal to 40° and more preferably between 20° and 40°. In a preferred embodiment, an angle of less than 40° has proven to be particularly suitable in practical use. With that, it was possible to achieve a particularly small installation space for the device.

Advantageously, the second beam splitter is arranged so that object radiation, which leaves the selection hologram without being diffracted, impinges on the second beam splitter, but is passed on in such a manner that it passes by the determination area of the detector. Scattered light passes through the selection hologram without being diffracted and therefore does not impinge on the determination area of the detector. Thus, it cannot falsify the measurement result.

In a preferred embodiment, the laser emitters are arranged at a distance from one another. The ratio of the wavelength difference between the wavelengths of the individual laser emitters to the distance between the laser emitters ranges preferably from $1:10^6$ to $1:10^3$, preferably from $1:10^5$ to $1:(5*10^5)$. These values are typical for a central wavelength $\lambda_0 = 900$ nm and can deviate for other wavelengths.

For example, the laser emitters can be arranged on an emitter chip and spaced apart from one another at least in the horizontal direction. Laser radiation of the individual laser emitters, and thus with different wavelengths, impinges on the first beam splitter at different incidence angles.

The device preferably has a collimating lens, which collimates the laser radiation and directs it in the direction of the first beam splitter. It is disposed between the laser emitters and the first beam splitter. The first beam splitter comprises an optical grating, which deflects the incident laser radiation depending on its wavelengths and at a given ratio of the wavelength difference to the distance between the laser emitters in such a manner that the collimated illumination radiation of the laser emitters leaves the beam splitter with a maximum angular spectrum range of 0 to 4 mrad and preferably of 0.5 to 3 mrad, relative to a central beam. Optionally, the first beam splitter may be designed as a beam splitter cube.

By means of the first beam splitter, a narrowing of the angular dispersion as well as a maximum light intensity is achieved. Preferably, a division of the laser radiation into a reference radiation and an illuminating radiation takes place in such a manner that the proportion of reference radiation is significantly smaller than the proportion of illuminating radiation. The proportion of reference radiation is particularly preferably below 40%, very preferably below 20%.

In the context of this disclosure, the term "central beam" is understood to be a laser beam, which is emitted from the center of an optical device, in the above case the first beam splitter.

Advantageously, the device has a Dammannn grating, which splits the illumination radiation of a laser emitter into a plurality of vertically arranged, collimated illuminating beams lying next to one another. With reference to the Figures, "vertical" is understood to be "perpendicular to the plane of the sheet" in the present text and "horizontal" as "in the plane of the sheet." The illuminating beams then impinge on the object to be detected as illuminating spots and are preferably arranged next to one another such that they jointly form a lighting strip. One of ordinary skill in the art is aware that illuminating radiation, which impinges on highly scattering materials, such as, for example, a tooth, causes scattered light and thus speckle noise. It has been found that the use of illuminating spots and thus an incomplete illumination of an illuminating strip can significantly reduce speckle noise.

It is particularly preferred if the device has a fanning hologram, which is disposed downstream from the first beam splitter or behind the optional Dammannn grating in the direction of the beam. The fanning hologram fans the illuminating beams in horizontal direction in such a manner that a plurality of illuminating strips impinge on the object. Preferably, a central strip, particularly preferably two edge strips and a central strip are produced. The illuminating strips preferably impinge on the object horizontally next to each other. By using a plurality of illuminating strips, a tilting of the device relative to the object can also be recognized.

The fanning hologram is preferably designed to deflect the illuminating strips horizontally away from the optical axis. The illuminating strips are deflected in such a manner that they meet the selection hologram and are diffracted from the selection hologram in the direction of the optical axis, preferably fulfilling the respective Bragg condition. Preferably, the selection hologram compensates for the deflection of the illuminating strips by the fan hologram. In addition, the selection hologram can also correct the angular dispersion (beam spread) of the central strip, so that the illuminating radiation of the central strip is collimated.

In the context of this disclosure, it has been found that the illuminating radiation should be collimated as completely as possible, before it impinges on the fanning hologram or the selection hologram. Only in this way can it be guaranteed that the radiation is fanned out completely and deflected by the two holograms. In addition, it has proven to be particularly advantageous if the individual optical devices, which are disposed between the laser emitters and the fanning or the selection hologram, are matched and aligned exactly with one another. This ensures that the illuminating radiation is coupled completely into the two holograms. However, the necessary adjustment effort may be considerable in some cases.

In an alternative embodiment, the device may have an optical fiber chip, which comprises the first beam splitter and into which the laser radiation of the laser emitters is coupled. The optical waveguide chip includes an arrayed waveguide grating. This is designed in such a manner that the illuminating radiation of the individual laser emitters is combined in an optical fiber. The use of the optical waveguide chip eliminates the adjustment work of the optical components, which are replaced by the waveguide chip. Overall, a simplified design of the device results from the optical waveguide chip. Optionally, the optical waveguide chip may comprise a multiple splitter, which splits the illuminating radiation of the individual optical fibers into a plurality of illuminating spots. In this case the Dammannn grid may be omitted.

Advantageously, the device is designed as a cavity scanner for the three-dimensional detection of a cavity with an inner wall. As a result, the range of application of the device according to this disclosure expands beyond the recognition of three-dimensional outer surfaces of an object.

Particularly preferably, the device comprises one or more wavefront rotators. They are designed to rotate the illuminating strips. The illuminating strips are rotated in such a manner that they are disposed transversely to the direction of the beam, particularly radially to the optical axis. Preferably, the wavefront rotators are positioned parallel to the optical axis. One wavefront rotator is preferably used for each illuminating strip.

Advantageously, the rotated illuminating strips are distributed uniformly, so that the angles between in each case two adjacent illuminating strips are identical. Preferably, three illuminating strips are used, which are arranged at an angle of 120° to one another. When four illuminating strips are used, they are arranged at an angle difference of 90° to one another. In the context of this disclosure, it has been found that, when a cavity is detected, a uniform distribution of the illuminating strips in the circumferential direction leads to a faster and more reliable detection of the cavity.

Particularly preferably, a prism, especially a triple prism, is disposed downstream from the wavefront rotators in the direction of the beam. The triple prism directs three illuminating strips, corresponding to the prism, by 90° in such a manner that each of the illuminating strips runs parallel to the optical axis.

Preferably, the illuminating strips, deflected by the prism or triple prism, impinge on the inner wall of a cavity parallel to the longitudinal axis thereof. This is the case if the cavity is constructed cylindrically or approximately cylindrically and thus rotationally symmetrically with respect to its longitudinal axis. If, for example, three illuminating strips with uniform angular spacing are used, the inner wall of the cavity can be covered completely by the distance of the illuminating strip by rotating the device by 120°. If the device is moved simultaneously along the longitudinal axis, the entire inner wall can be scanned spirally. The advantage of illuminating strips disposed uniformly in the circumferential direction when a cylindrical cavity is being detected is that, even if the device is positioned outside the longitudinal axis of the cavity, this does not lead to an appreciably poorer result in practice. By using a plurality of illuminating strips, an eccentric position of the device can be calculated and the results of the measurement can be corrected accordingly.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 3 shows a section of a third embodiment of the device according to this disclosure;

FIG. 4a shows a projection of the illuminating strips according to a selection hologram of the device of FIG. 3; and FIG. 4b shows a projection of the illuminating strips of the wavefront rotators of the device of FIG. 3.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
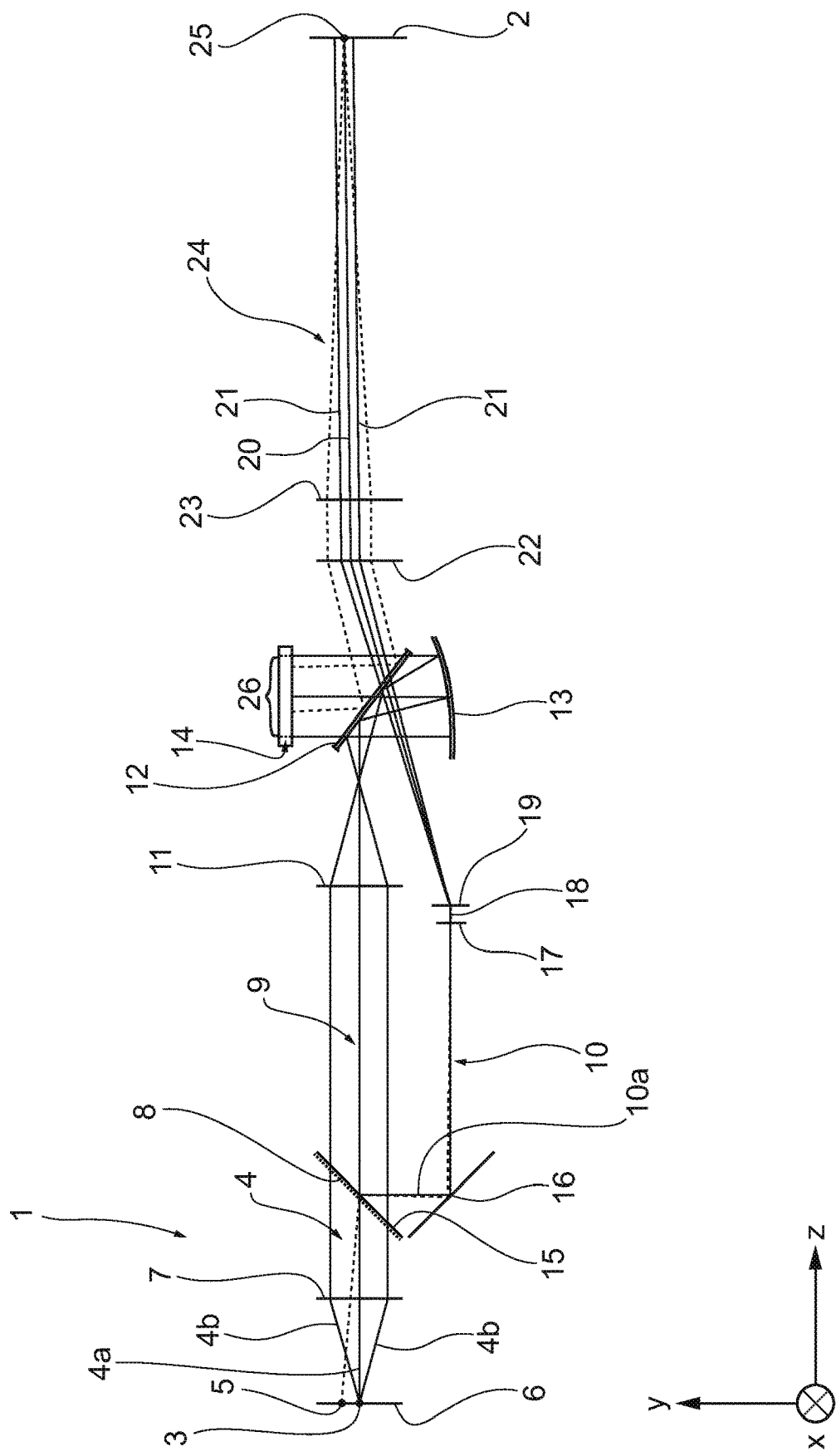
FIG. 1 shows a diagrammatic representation of a device according to the this disclosure according to a first embodiment.

FIG. 1 shows a device 1 for detecting a 3D structure of an object 2. The basic function of the device 1 is described in EP 2 796 938 B1, which is hereby incorporated by reference in its entirety.

For a simplified explanation of the device according to this disclosure, a coordinate system, which is illustrated in FIG. 1 and has X, Y and Z axes, is to be defined. While the X axis is the vertical (perpendicular to the plane of the sheet) and the Y axis the horizontal one (in the plane of the sheet), the Z axis points in the direction of beam propagation, i.e., from left to right in the direction of the object 2 in FIG. 1.

The device 1 comprises a first laser emitter 3, which generates laser radiation 4 with a first wavelength, and a second laser emitter 5, which generates laser radiation at a second wavelength (not shown). The two laser emitters, 3, 5, are arranged on an emitter chip 6 and emit laser radiation of different wavelengths. They are spaced apart along the Y axis. The ratio of the wavelength difference between the wavelengths of the individual laser emitters 3, 5 to the distance of the laser emitters 3, 5 preferably ranges from $1\times10^{-6}$ to $1\times10^{-3}$. In particular, the ratio preferably is in the range of $1\times10^{-5}$ to $5\times10^{-5}$.

A central beam 4a and two edge beams 4b of the laser radiation 4 are shown in FIG. 1. The laser radiation 4 passes through a collimating lens, which is denoted as a first lens 7 and collimates the laser radiation, i.e., parallelizes it. Depending on the distances between the laser emitters 3, 5 along the Y axis, the collimated laser radiation of the laser emitters 3, 5, after passing through the first lens 7, have different angles relative to the Z axis. For a simplified representation, only the laser radiation 4 of the first laser emitter 3 is shown in FIG. 1. This runs parallel to the Z-axis downstream from the first lens 7.

A first beam splitter 8, which splits the laser radiation 4 of the laser emitters 3, 5 into a reference radiation 9 and an illuminating radiation 10, is disposed in the direction of the beam (Z axis) downstream from the first lens 7 (collimating lens). Preferably, the dividing ratio is 1 to 9. 10% of the laser radiation 4 becomes reference radiation 9; 90% of the laser radiation 4 is deflected as the illuminating radiation 10 at a defined angle. The reference radiation 9 is thus attenuated to 10% of the laser radiation 4.

The reference radiation 9, which passes through the beam splitter virtually without deflection, is directed by a second lens 11 to a second beam splitter 12, which directs it to a detector 14 via a hollow mirror 13. Depending on the distances between the laser emitters 3, 5 on the emitter chip 6, the reference radiation 9 of the individual laser emitters 3, 5 impinges on the detector 14 at different incidence angles. The second beam splitter 12 can be designed as a semi-transparent mirror.

The first beam splitter 8 comprises an optical grating 15, which deflects parts of the incident laser radiation 4 as illuminating radiation 10 depending on the wavelengths of the laser beam 4 and depending on the ratio of the wavelength difference to the distance between the laser emitters on the emitter chip 6. The illuminating radiation 10 is represented in FIG. 1 by a central beam 10a. The edge beams have been omitted for the sake of simplicity.

The deflected central beam 10a of the laser emitter 3 is deflected by 90° and runs along the Y axis. The optical grating 15 deflects the laser radiation 4 of the remaining laser emitters 5 in such a manner that the collimated illuminating beams of the remaining laser emitters 5 leave the first beam splitter 8 with a maximum angular spectrum range relative to the central beam 10a of 0 to 4 mrad, preferably of 0.5 to 3 mrad, particularly preferably of 1 to 2 mrad.

The illuminating radiation 10 is directed onto a Dammann grating 17 via a deflecting mirror 16. The Dammann grating 17 divides the illuminating radiation 10 of a laser emitter 3, 5 into a plurality of collimated illuminating beams 18, which lie side by side vertically (along the X axis) and collide with the object 2 as illuminating spots. The illuminating spots are arranged side by side in such a manner that together they form an illuminating strip.

The device further comprises a fanning hologram 19, which fans the illuminating beams 18 in the horizontal direction (Y direction) in such a manner that a plurality of illuminating strips (not shown), namely a center strip and two edge strips, impinge on the object 2. The fanned illuminating beams 18 are shown simply as a center strip beam 20 and two edge strip beams 21 in FIG. 1. These are deflected horizontally away from the optical axis (horizontal) by the fanned hologram 19 in such a manner that the illuminating strips impinge on a selection hologram 22. The selection hologram 22 deflects the illuminating strips toward the optical axis, i.e., in the direction of the Z axis.

As can be seen in FIG. 1, the center strip beam 20 is deflected by the selection hologram 22 in such a manner that it extends along the Z axis and thus along the optical axis of the selection hologram 22 in the direction of the object 2. The selection hologram 22 can completely compensate for the deflection of the center strip beam 20 by the fanned hologram 19. With regard to the two edge strip beams 21, the deflection by the fanned hologram 19 cannot be compensated for completely by the selection hologram 22. However, these minimal displacements in the Y-direction do not play a role in practice and can mostly be neglected if the design is proper.

A third lens 23, which preferably focuses the center strip beam 20 and the two edge strip beams 21 so weakly, that these are parallel to the optical axis, that is to say parallel to the Z axis and extend parallel to one another and are preferably almost collimated in the measuring range, is located in the beam direction downstream from the selection hologram 22. The beams preferably are focused slightly by the third lens 23, as a result of which they are preferably tapered and have a beam waist preferably of about 50 μm to 300 μm. The illuminating radiation 10 then impinges on the object 2 in a center strip and two edge strips.

In the context of this disclosure, it has been found that a coaxial (aligned) arrangement of the two lenses 7, 11 relative to the selection hologram 22 and the third lens 23 is particularly advantageous. Installation space can be saved in this way. In this arrangement, after passing through the selection hologram 22, the central beam 4a of the laser radiation 4 and the center strip beam 20 run coaxially and aligned with one another. This is made possible by the two holograms 19, 22, which align the illuminating radiation, after reflection at the deflecting mirror 16, coaxially again to the central beam 4a.

Preferably, the device has a diameter of at most 40 mm in the region of the detector 14 and the hollow mirror 13. Further preferably, the diameter of the device 1 in the region of the third lens 23 is at most 15 mm and in the region of its object-side end is at most 12 mm. The distance in the Z direction between the third lens 23 and the object-side end of the device 1 preferably is about 80 mm to 120 mm, particularly preferably about 90 mm. Other dimensions are possible.

As shown in FIG. 1, the illuminating radiation 10 is reflected at object 2 as object radiation 24. In FIG. 1, the object radiation 24 is shown by way of example as at starting out from an object point 25 of the object 2 (dashed line). The object point 25 can be viewed simply as a point light source. The object radiation 24 extends from the object point 25 in the direction of the third lens 23 and, collimated by the latter, impinges on the selection hologram 22.

The selection hologram 22 is a volume hologram. It exclusively directs object radiation 24, which impinges on the selection hologram 22 at a predetermined incident angle range and fulfills the Bragg equation in such a manner that, on its further path, the object radiation 24 falls onto a determination area 26 of the detector 14. The object radiation 24 preferably impinges on the determination area 26 of the detector 14 at an incidence angle, which is smaller than a predefined determination angle range. Radiation, incident in this way, can be evaluated by an evaluation unit (not shown). The second beam splitter 12 can be arranged in such a manner that the object radiation 24, deflected downwards by the selection hologram 22 in FIG. 1, impinges on the second beam splitter 12 and is deflected in the direction of the determination area 26 of the detector 14. Preferably, the angle between the second beam splitter and the Z axis results from the angle of inclination of the selection hologram and the fact that the collimated light should fall as perpendicularly as possible on the detector. Particularly preferably, the second beam splitter can be arranged tilted relative to the Z axis by an angle of less than 40°.

Other object radiation 24, deflected from the object 2, such as scattered light, which impinges on the selection hologram 22 outside of the incidence angle area and therefore does not fulfill the Bragg equation, passes through the selection hologram 22 without being diffracted. The second beam splitter 12 is arranged in such a manner that the undiffracted object radiation 24 impinges on the second beam splitter 12 and is reflected in such a manner that it impinges on the determination area 26 of the detector 14 either at an angle greater than the detection angle range or passes by the determination area 26 of the detector 14. It can impinge on the detector 14 entirely outside of the determination area 26, for example still in a detection area of the detector 14, or can be deflected past the detector 14.

The extent of the incidence angle range depends on the parameters of the Bragg equation, i.e., inter alia, on the wavelength of the object radiation and the distance between two parallel grating planes in the selection hologram 22. Consequently, there are different incidence angle ranges for the different object radiation 24 of the different laser emitters 3, 5. The incidence angle ranges are defined between the Z axis and the Y axis and between the X axis and the Z axis. The incidence angle ranges between the X and Z axes are larger than those between the Z and Y axes. The incidence angle ranges between the X and Z axes amount to several 100 mrad, so that the object radiation 24 is passed over the whole length of the individual illuminating strips onto the detector 14. The object radiation 24, which is directed onto the determination area 26 of the detector 14, then interferes with the reference radiation 9 of the same wavelength. The resulting interference patterns are recorded by the detector 14 and enable a statement about the three-dimensional structure of the object 2.

It is understood that the Bragg equation does not only have to be fulfilled by the object radiation 24 in order to be directed by the selection hologram 22 onto the second beam splitter 12. The illuminating radiation 10, which impinges on the fanned hologram 19 or is deflected by the latter onto the selection hologram 22 respectively, must also fulfill the Bragg equation. Only in this case do the fan hologram 19 and the selection hologram 22 deflect the illumination radiation as described above. The individual optical devices in the direction of beam propagation upstream from the fanned hologram 19 must be aligned precisely with one another and adjusted. The illumination radiation 10 of the laser emitters 3, 5 must run in the smallest possible angular spectrum range relative to the central beam 10*a*, preferably in an angular spectrum ranging from 0.5 to 3 mrad. This refers to the deviation of the central beams of the individual emitters from the central beam 10*a* (corresponds to the central beam of the central emitter 3).

Figure 2:
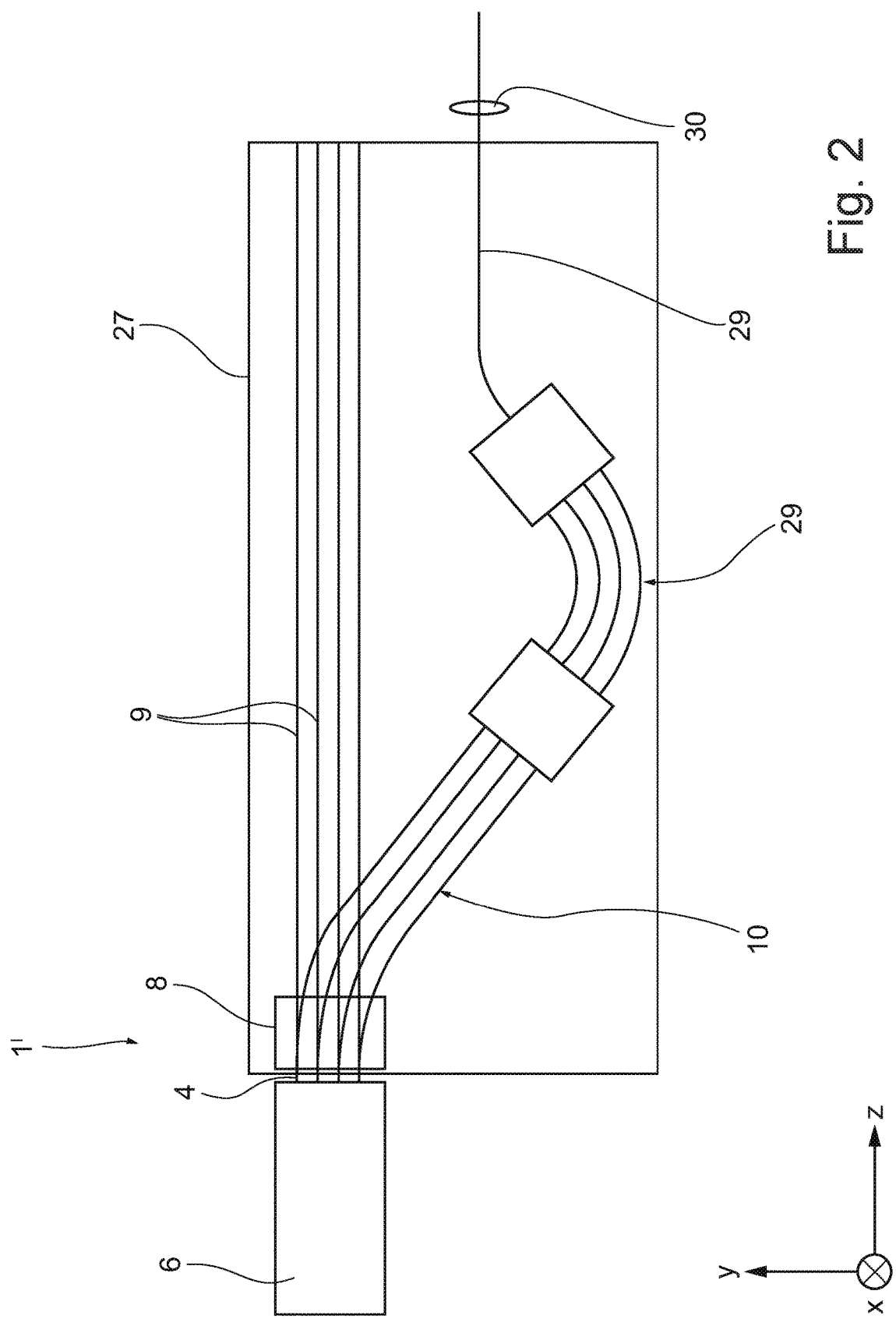
FIG. 2 shows a section of a second, alternative embodiment of the device according to this disclosure.

FIG. 2 shows a section of a second embodiment of the device according to this disclosure (FIG. 1). The device 1' comprises a laser module, designed as an emitter chip 6, with, for example, a total of four laser emitters (not shown) and a waveguide chip 27, into which the laser radiation 4 of the laser emitters is coupled. The waveguide chip 27 comprises the first beam splitter 8 (of FIG. 1), which is designed as a quadruple beam splitter and divides the laser radiation 4 of each laser emitter into a reference radiation 9 and the illuminating radiation 10. The reference radiation 9 passes through the waveguide chip 27 unchanged. If the emitter chip 6 (laser module) comprises a different number of emitters, the waveguide chip 27 and the beam guide 8 are modified correspondingly and correspond to the emitter chip 6.

The waveguide chip 27 furthermore comprises an arrayed waveguide grating 28, which combines the illuminating radiation 10 of the individual laser emitters into an optical fiber 29. After emerging from the waveguide chip 27, the illuminating radiation 10 impinges on the lens 30, which passes it on onto the Dammannn grating 17 of FIG. 1.

With respect to the reference radiation 9, starting from the laser emitters, the components of the device 1', shown in FIG. 2, replace all optical components in the direction of the beam path as far as the second lens 11 (cf. FIG. 1). With respect to the illuminating radiation 10, starting from the laser emitters, all optical components in the direction of the beam path as far as the Dammannn grating 17 are replaced. The remaining components of the device according to this disclosure are identical with those of the device 1'.

FIG. 3 shows a section of a third embodiment of the device. The device 1" is a cavity scanner for the three-dimensional detection of a cavity 31 having an inner wall 32. The device 1" differs from that in FIG. 1 by wavefront rotators 33. These rotate the illuminating strips such that they are arranged radially relative to the optical axis. The wavefront rotators 33 are disposed in the direction of the beam path downstream from the selection hologram 22 and downstream from the third lens 23. For a simplified illustration, only two wavefront rotators 33 are shown in FIG. 3, which rotate the illumination of two edge strip beams 21.

FIG. 4*a* shows a section through the beam path at the position marked in FIG. 3 with the letter $S_1$ in the direction of the beam path downstream from the selection hologram 22. As can be seen in FIG. 4*a*, the illuminating radiation 10 was fanned out by means of the Dammannn grating 17 and the fanned hologram 19 into three illuminating strips 34, which are arranged parallel to one another. Two of the illuminating strips 34 are arranged next to one another. The third illuminating strip 34 is located centrally above the other two illuminating strips 34.

FIG. 4*b* shows a section through the beam path at the point $S_2$ indicated in FIG. 3 after the illuminating radiation 10 has passed through the wavefront rotators 33. As can be seen in FIG. 4*b*, the rotated illuminating strips are preferably distributed uniformly, so that the angles between two adjacent illuminating strips each are identical. Preferably, all three illuminating strips 34 are disposed at an angle of 120° to one another.

A triple prism 35, which deflects the three illuminating strips 34 by 90°, is disposed downstream from the wavefront rotators 33 in the beam propagation direction. The illuminating strips 34 then each extend parallel to a longitudinal axis of the cavity 31 and meet the inner wall 32 thereof. By rotating the device 1" by 120°, the inner wall can be detected over its entire circumference via the segment of the illuminating strips 34 extending in the Z direction. If the device 1" is moved simultaneously into the cavity 31 along the longitudinal axis 36, the entire inner wall 32 of the cavity 31 can be scanned in a helical manner.

Alternatively, it is also possible to use more than three illuminating strips 34, for example, four illuminating strips 34 with an angular difference of 90° from one another.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A device for determining a 3D structure of an object, comprising:
    first and second laser emitters which generate laser radiation with first and second different wavelengths, respectively;
    a first beam splitter, which splits the laser radiation of each laser emitter into a reference radiation and an illuminating radiation, wherein the illuminating radiation is adapted to impinge on the object to be measured, be reflected by the object as object radiation, and interfere with the reference radiation to form interference patterns;
    a detector adapted to receive the interference patterns;
    a selection hologram configured to exclusively deflect object radiation which impinges on the selection hologram within a predefined incidence angle range, wherein the deflected object radiation impinges on a determination area of the detector at an angle within a determination angle range; and
    wherein the selection hologram is further configured to pass object radiation which impinges on the selection hologram outside of the incidence angle range undiffracted, wherein the undiffracted radiation either passes by the determination area of the detector or impinges on the determination area at an angle outside the determination angle range.

2. The device according to claim 1, wherein the selection hologram is a volume hologram, wherein the object radiation which impinges on the selection hologram within a predefined incidence angle range fulfills the Bragg equation, and wherein the undiffracted radiation does not fulfill the Bragg equation.

3. The device according to claim 1, wherein only object radiation that impinges on the determination area at an angle within the determination angle range is evaluated by an evaluation unit.

4. The device according to claim 1, further comprising a second beam splitter which is hit by the object radiation deflected by the selection hologram.

5. The device according to claim 4, wherein the second beam splitter is arranged such that the object radiation which leaves the selection hologram without being diffracted impinges on the second beam splitter, is reflected, and passes by the determination area of the detector.

6. The device according to claim 1, wherein the first and second laser emitters are arranged at a distance from one another, wherein a ratio of the difference between the wavelengths of the first and second laser emitters to the distance between the first and second laser emitters ranges from 10-6 to 10-3.

7. The device according to claim 6, further comprising a lens configured to collimate and direct the laser radiation to the first beam splitter, wherein the first beam splitter comprises an optical grating which deflects parts of the incident laser radiation as a function of wavelength and, at a given ratio of wavelength difference to the distance between the laser emitters, as illuminating radiation such that the collimated illuminating beams of the laser emitters leave the beam splitter with a maximum angular spectrum range relative to a central beam ranging from 0 to 4 mrad.

8. The device of claim 7, wherein the collimated illuminating beams of the laser emitters leave the beam splitter with a maximum angular spectrum range relative to the central beam ranging from 0.5 to 3 mrad.

9. The device according to claim 1, further comprising a Dammann grating configured to split the illuminating radiation into several collimated illuminating beams disposed vertically next to one another and impinge on the object as illuminating spots.

10. The device according to claim 9, wherein the spots together form an illuminating strip.

11. The device according to claim 9, further comprising a fanned hologram configured to fan the illuminating beams in the horizontal direction such that several illuminating strips impinge on the object.

12. The device according to claim 11, wherein the illuminating strips preferably comprise a center strip.

13. The device according to claim 12, wherein the illuminating strips further comprise two edge strips.

14. The device according to claim 11, wherein the fanned hologram is configured to deflect the illuminating strips horizontally away from the optical axis of the fanned hologram such that the illuminating strips impinge on the selection hologram and are diffracted by the selection hologram toward the optical axis of the selection hologram.

15. The device according to claim 14, wherein the illuminating strips fulfill the Bragg equation.

16. The device according to claim 1, further comprising an optical waveguide chip, which comprises the first beam splitter and into which the laser radiation of the laser emitters is coupled.

17. The device according to claim 16, wherein the optical waveguide chip comprises an arrayed waveguide grating configured to combine the illuminating radiation of the individual laser emitters into an optical fiber.

18. The device according to claim 1, wherein the device is configured as a cavity scanner for the three-dimensional detection of a cavity having an inner wall.

19. The device according to claim 1, further comprising wavefront rotators configured to rotate illuminating strips such that they are disposed transversely to the beam propagation direction of the illuminating radiation.

20. The device of claim 19, wherein the wavefront rotators are configured to rotate the illuminating strips such that the illuminating strips are disposed radially to the optical axis of the selection hologram.

21. The device according to claim 20, wherein the rotating illuminating strips are distributed uniformly such that the angles between any two adjacent illuminating strips are identical.

22. The device of claim 21, wherein the illuminating strips comprise three illuminating strips disposed at an angle of 120° to one another.

23. The device according to claim 20, further comprising a triple prism arranged downstream from the wavefront rotators in the direction of the illuminating beam path, the triple prism configured to deflect by 90° three illuminating strips that correspond with the triple prism such that the illuminating strips each extend parallel to the optical axis of the selection hologram.

24. The device according to claim 23, wherein the illuminating strips deflected by the triple prism are configured to impinge on an inner wall of a cavity parallel to the longitudinal axis of the cavity.

\* \* \* \* \*